United States Patent [19]

Michl et al.

[11] Patent Number: 5,731,470
[45] Date of Patent: Mar. 24, 1998

[54] WEAKLY NUCLEOPHILIC ANIONS

[75] Inventors: Josef Michl; Benjamin T. King, both of Boulder, Colo.; Zbyněk Janoušek, Stare Mesto, Czech Rep.

[73] Assignee: Board of Regents of the University of Colorado, Boulder, Colo.

[21] Appl. No.: 628,357

[22] Filed: Apr. 5, 1996

Related U.S. Application Data

[63] Continuation-in-part of Ser. No. 416,395, Apr. 5, 1995, abandoned.

[51] Int. Cl.⁶ ............................................. C07F 5/02
[52] U.S. Cl. ................................. 564/9; 564/10; 568/3; 568/4; 568/5
[58] Field of Search ............................ 564/9, 10; 568/3, 568/4, 5

[56] References Cited

U.S. PATENT DOCUMENTS

| | | | |
|---|---|---|---|
| 3,109,031 | 10/1963 | Goldstein | 260/606.5 |
| 4,097,662 | 6/1978 | Huskins | 526/217 |
| 4,100,199 | 7/1978 | Dunks | 260/608.5 B |
| 4,153,672 | 5/1979 | Dunks | 423/287 |
| 5,278,119 | 1/1994 | Turner | 502/155 |
| 5,317,058 | 5/1994 | Dougherty | 525/54 |
| 5,489,673 | 2/1996 | Wilbur | 536/17.1 |

OTHER PUBLICATIONS

Bahr, S.R. and Boudjouk, P. (1992), "Trityl tetrakis(3, 5-bis(trifluoromethyl)-phenyl)borate: a new hydride abstraction reagent," *J. Org. Chem.* 57:5545–5547.

Bahr, S.R. and Boudjouk, P. (1993) "Stable silylnitrilium ions," *J. Am. Chem. Soc.* 115:4512–4519.

Bregadze, V. (1992), "Dicarba-*closo*-dodecaboranes $C_2B_{10}H_{12}$ and Their Derivatives," *Chem. Rev.* 92:209–223.

Grimes, Russell N. (1992), "Boron–Carbon Ring Ligands in Organometallic Synthesis," *Chem. Rev.* 92:251–268.

Gupta et al. (1987) "Spin coupling in admixed intermediate-spin iron(III) porphyrin dimers: crystal structure, Mössbauer, and susceptibility study of $Fe(TPP)(B_{11}CH_{12})\cdot C_7H_8$," *Inorg. Chem.* 26:3022–3030.

Heřmánek, Stanislav, (1992), "¹¹B NMR Spectra of Boranes, Main-Group Heteroboranes, and Substituted Derivatives. Factor Influencing Chemical Shifts of Skeletal Atoms, " *Chem. Rev.* 92:325–362.

King, Benjamin et al. (1996) "Dodecamethylcarba-*closo*-dodecaborate(-) Anion, $CB_{11}Me_{12}^-$," *J. Am. Chem. Soc.* 118:3313–3314.

Ivanov, S. V. et al. (1995) "Regioselective Fluorination of $CB_{11}H_{12}^-$,"*Inorg. Chem.* 34, 6419–6420.

Jeínek et al. (1986), "Chemistry of compounds with the 1-carba-*closo*-dodecaborane(12) framework," *Coll. Czech. Chem. Commun.* 51:819–829.

Jelínek et al. (1993), "New weakly coordinating anions. 2. derivatization of the carborane anion $CB_{11}H_{12}^-$," *Inorg. Chem.* 32:1982–1990.

Jiang, W. et al. (1995), "A Camouflaged Icosahedral Carborane: Dodecamethyl—1, 12—dicarba-*closo*-dodecaborane(12) and Related Compounds," *Angew. Chem. Int. Ed. Engl.* 34, No. 12.

Knoth, W. (1967) "1—$B_9H_9CH^-$ & $B_{11}H_{11}CH^-$," *J.Am.Chem.Soc.* 89:1274–1275.

Lambert et al. (1993), "Crystal structure of a silyl cation with no coordination to anion and distant coordination to solvent," *Science* 260:1917–1918.

Lambert et al. (1994), "Silyl cations in the solid and in solution," *Organometallics* 13:2430–2443.

Leites, L. A. (1992), "Vibrational Spectroscopy of Carboranes and Parent Boranes and Its Capabilities in Carborane Chemistry," *Chem. Rev.* 92:279–323.

Li et al. (1991), "simple syntheses and alkylation reactions of 3–iodo–*o*–carborane and 9,12–diiodo–*o*–carborane," *Inorg. Chem.* 30:4866–4868.

Liston et al. (1987) "Donor-acceptor metal—metal bonding instead of methathesis with Vaska's compound and the silver(I) salt of the weakly coordinating anion $B_{11}CH_{12}$," *Inorg. Chem.* 26:2739–2740.

Liston, D.J. (1989) "Observations on silver salt metathesis reactions with very weakly coordinating anions," *J. Am. Chem. Soc.* 111:6643–6648.

Olah, G., Wade, K., Williams, R. (1991), "Electron Deficient Boron and Carbon Clusters," *Wiley–Interscience Pub.*, John Wiley & Sons, ISBN 0–471–52795–5.

Plešek et al. (1984), "A convenient preparation of 1—$CB_{11}H_{12}^-$ and its C-amino derivatives," *Coll. Czech. Chem. Commun.* 49:1559–1562.

Plešek, J. (1992), "Potential Applications of the Boron Cluster Compounds," *Chem. Rev.* 92:269–278.

Reed et al. (1993), "Closely approaching the silylium ion $(R_3Si^+)$," *Science* 262:402–404.

Shelley et al. (1985) "n¹–benzene coordination: the synthesis and x–ray crystal structure of a novel silver salt of the weakly coordinating carborane anion $B_{11}CH_{12}^-$," *J. Am. Chem. Soc.* 107:5955–5959.

Shelley et al. (1986) "The least coordinating anion," *J. Am. Chem. Soc.* 108:3117–3118.

Stibr, B. (1992), "Carboranes Other than $C_2B_{10}H_{12}$," *Chem. Rev.* 92:225–250.

Strauss et al. (1986) "Teflate $(OTeF_5^-)$ as a unique ligand for metal complexes: structure of $[TlOTeF_5(1,3,5-(CH_3)_3C_6H_3)_2]_2$, a thallium(I) complex with neutral arene ligands," *Inorg. Chem.* 25:3850–3851.

(List continued on next page.)

*Primary Examiner*—Shailendra Kumar
*Attorney, Agent, or Firm*—Greenlee, Winner & Sullivan, P.C.

[57] ABSTRACT

Substituted borate and carborate anions having unusual properties of being exceptionally weakly nucleophilic and being soluble in non-polar solvents. One-electron oxidation of the anions yields the corresponding radicals. The compounds are useful, e.g., as electrolytes, catalysts, and electrochromic materials.

32 Claims, No Drawings

OTHER PUBLICATIONS

Strauss, S.H. (1993), "The search for larger and more weakly coordinating anions," *Chem. Rev.* 93:927–942.

Williams, R.E. (1992), "The Polyborane, Carborane, Carbocation Continuum: Architectural Patters," *Chem. Rev.* 92:177–207.

Wong, E., et al. (1980) "Boron Halide Clusters and Radicals: Synthesis and Interconversions of the Three Oxidation States of a Nine–Boron Polyhedron," *Inorg. Chem.* 19:451–455.

Xie, Zuowei et al. (1996), "Approaching the Silylium $(R_3Si^{3o})$ Ion: Trends with Hexahalo (Cl, Br, I) Carboranes as Counterions," *J. Am. Chem. Soc.* 18:2922–2928.

Xie et al. (1993) "A weakly coordinating anion: approaching the silylium (silicenium) ion," *J. Chem. Soc., Chem. Comun.*, pp. 384–386.

Zakharkin et al. (1982), "Synthesis of B–organo–substituted 1,2–, 1,7–, and 1, 12–dicarbaclosododecaboranes(12)," *J. Organomet. Chem.* 226:217–222.

WEAKLY NUCLEOPHILIC ANIONS

CROSS REFERENCE TO RELATED APPLICATIONS

This application is a continuation-in-part of U.S. patent application Ser. No. 08/416,395, filed Apr. 5, 1995, now abandoned which is incorporated in its entirety by reference herein.

The U.S. Government may have rights in the invention based on grant support from National Science Foundation Grant No. CHE 9318469.

FIELD OF THE INVENTION

The invention relates to the field of chemistry, and in particular to substituted and derivatized polyhedral borate and carborate anions and radicals useful in a variety of applications, for example, as weakly nucleophilic anions and/or as oxidizing agents.

BACKGROUND OF THE INVENTION

There has been a consistent effort to develop anions that are very weakly nucleophilic. Preferably, such compounds should also contain no nucleophilic coordination sites such as exposed lone pairs of electrons, aromatic rings, multiple bonds or hydridic hydrogens. Salts of such compounds should also be soluble in inert, low-polarity solvents. None of the known weakly nucleophilic anions meet these criteria. (For a recent review, see Strauss, S. H. (1993) *Chem. Rev.* 93:927–942).

Among the known anions displaying some of the above properties, certain deltahedral closo-carborate anions ($CB_{11}H_{12}^{1-}$) have been shown to be both weakly coordinating and weakly nucleophilic (Reed, C. A. et al. (1993) *Science* 262:402; Xie et al., (1993) *J. Chem. Soc., Chem. Comm.* pp. 384–386 Shelley, K. et al. (1985) *J. Am. Chem. Soc.* 107:5955; Strauss, S. H. et al. (1986) *Inorg. Chem.* 25:3850; Liston, D. J. (1989) *J. Am. Chem. Soc.* 111:6643; Gupta, G. P. et al. (1987) *Inorg. Chem.* 26:3022; Liston, D. J. et al. (1987) *Inorg. Chem.* 26:2739; Shelley, K. et al. (1986) *J. Am. Chem. Soc.* 108:3117). Mono-alkylated closo-dodecaborates substituted at the 1-position are known. (Jelinek, T. et al. (1993) *Inorg. Chem.* 32: 1982). Several mono- and poly-halogenated derivatives of the closo-carborate anions $CB_{11}H_{12}^{1-}$ have been synthesized. (Ivanov, S. V. et al. (1995) *Inorg. Chem.* 64: 6419.)

1,12-Dimethyl-1,12-dicarba-closo-dodecaborane was permethylated via a methyl triflate - triflic acid mixture and 1,12-dicarba-closo-dodecaborane was methylated at all 10 boron vertices in an analogous reaction (Jiang, W. et at. (1995) *Angew. Chem. Internal. Ed. Engl.* 34: 1332). Small amounts of undecamethylcarborane, in which all boron vertices and one carbon vertex were methylated, appeared to be formed in the latter reaction. Under such conditions, we have found that the much more reactive monocarbaborane (1–) anions, e.g. $CB_{11}H_{12}^{1-}$, were converted into products other than the corresponding fully methylated anions, e.g. $CB_{11}Me_{12}^{1-}$.

We are unaware of any prior reports of characterization and isolation of polyhedral boranyl or carboranyl radicals. Irreversible one-electron oxidation of $CB_{11}H_{12}^{1-}$ has been reported (Jelinek, T. et al. (1993) *Inorg. Chem.* 32: 1982). This and similar reactions may proceed through radicals.

Polyhedral boranyl and carboranyl radicals are useful as oxidizing agents. Polyhedral boranyl and carboranyl radicals have applications, in combination with their reduced forms (the corresponding anions formed by one-electron reduction), as electrochromic materials and in batteries and conducting polymers.

SUMMARY OF THE INVENTION

The present invention provides methods for making polyhedral carborate and borate anions and carboranyl and boranyl radicals multiply substituted with hydrocarbon, halogenated-hydrocarbon, derivatized hydrocarbon, and derivatized halogenated-hydrocarbon substituents. The remaining vertices can contain hydrogens or halogens. A variety of salts of substituted polyhedral carborate and borate anions can also be prepared using the methods of this invention.

More specifically, the present invention provides the salts of closo-borate and carborate anions and hemicloso-boranyl and -carboranyl radicals multiply substituted with hydrocarbon, halogenated-hydrocarbon, halogen, derivatized hydrocarbon, and derivatized halogenated-hydrocarbon substituents. A variety of salts of these anions, such as $Li^+$ salts, are provided by this invention. The hydrocarbon substituents of these anions and radicals include linear or branched alkyl, alkenyl or alkynyl groups and halogenated-hydrocarbon groups. Anions and radicals of this invention also include those in which any one of the hydrocarbon or halogenated-hydrocarbon substituents are derivatized to contain a variety of functional groups. These substituents can be derivatized with any of the following functionalities: mine, cyano, hydroxyl, thiol, carbonyl, carboxylate or carboxylic acid, halogen, epoxide, ester, amide, and ether. Anions of this invention are useful for applications where the combination of ionic character and weak-nucleophilicity is advantageous. Radicals of this invention have applications in batteries and electrochromic displays. The compounds of this invention can be used as precursors in the synthesis of other borate and carborate anions and boranyl and carboranyl radicals, including polymers and oligomers thereof. The properties and characteristics of the compounds of this inventions, including solubility and stability, can be adjusted by the choice of number and nature/identity of the substituent groups added. Table 1 gives exemplary deltahedral structures and molecular formulas of the closo-borate and closo-carborate anions and their corresponding hemicloso-radicals of this invention.

TABLE 1

Deltahedral Structures of Closo-Borate and Closo-Carborate Anions and their Corresponding Free Radicals Formed by One-Electron Oxidation

| # of Vertices | Molecular Formula | Deltahedral Structure |
|---|---|---|
| 6 | $B_6Y_6^{2-}$ borate anion $B_6Y_6^{1-}$ boranyl radical $CB_5Y_6^{1-}$ carborate anion $CB_5Y_6$ carboranyl radical | |
| 7 | $B_7Y_7^{2-}$ borate anion $B_7Y_7^{1-}$ boranyl radical $CB_6Y_7^{1-}$ carborate anion $CB_6Y_7$ carboranyl radical | |
| 8 | $B_8Y_8^{2-}$ borate anion $B_8Y_8^{1-}$ boranyl radical $CB_8Y_8^{1-}$ carborate anion $CB_7Y_8$ carboranyl radical | |

TABLE 1-continued

Deltahedral Structures of Closo-Borate and Closo-Carborate Anions and their Corresponding Free Radicals Formed by One-Electron Oxidation

| # of Vertices | Molecular Formula | Deltahedral Structure |
|---|---|---|
| 9 | $B_9Y_9^{2-}$ borate anion<br>$B_9H_9^{1-}$ boranyl radical<br>$CB_8H_9^{1-}$ carborate anion<br>$CB_8H_9$ carboranyl radical | |
| 10 | $B_{10}Y_{10}^{2-}$ borate anion<br>$B_{10}Y_{10}^{1-}$ boranyl radical<br>$CB_{10}Y_{10}^{1-}$ carborate anion<br>$CB_9Y_{10}$ carboranyl radical | |
| 11 | $B_{11}Y_{11}^{2-}$ borate anion<br>$B_{10}Y_{11}^{1-}$ boranyl radical<br>$CB_{10}Y_{11}^{1-}$ carborate anion<br>$CB_{10}Y_{11}$ carboranyl radical | |
| 12 | $B_{12}Y_{12}^{2-}$ borate anion<br>$B_{12}Y_{12}^{1-}$ boranyl radical<br>$CB_{11}Y_{12}^{1-}$ carborate anion<br>$CB_{11}Y_{12}$ carboranyl radical | |
| 13 | $B_{13}Y_{13}^{2-}$ borate anion<br>$B_{13}Y_{13}^{1-}$ boranyl radical<br>$CB_{12}Y_{13}^{1-}$ carborate anion<br>$CB_{12}Y_{13}$ carboranyl radical | |
| 14 | $B_{14}Y_{14}^{2-}$ borate anion<br>$B_{14}Y_{14}^{1-}$ boranyl radical<br>$CB_{13}Y_{14}^{1-}$ carborate anion<br>$CB_{13}Y_{14}$ carboranyl radical | |

In Table 1, Y can be either H (hydrogen) or R (hydrocarbon subtituents, halogenated-hydrocarbon subtituents, or derivatives thereof, or halogen, as noted above) at each vertex in the deltahedral structure. The anions of this invention include those of the formula $B_nH_{(n-x)}R_x^{2-}$ wherein n is an integer from 6 to 14 and x is an integer from 2 to n, and wherein each R, independent of each other R, is a hydrocarbon substituent, a halogenated-hydrocarbon subtituent, or a derivative of either, or a halogen; and the closo-carborate anions of molecular formula $CB_nH_{(n+1)-x}R_x^{1-}$ wherein n is an integer from 5 to 13 and x is an integer from 2 to n+1, and wherein each R, independent of each other R, is a hydrocarbon substituent, a halogenated-hydrocarbon subtituent, or derivatives of either, or a halogen.

In the case of borate anions and boranyl radicals, each vertex in the structures of Table 1 represents a boron atom. In the case of the carborate anions and carboranyl radicals in the structures of Table 1, one vertex represents a carbon atom and all of the other vertices represent boron atoms. In all of the compounds, each vertex can be substituted with any of the above mentioned R substituents. In the compounds of this invention, at least two vertices are substituted with R substituents other than hydrogen, that is with hydrocarbon substituents, halogenated-hydrocarbon subtituents, or derivatives thereof.

Most generally, the compounds of this invention are polyhedral, including borates and carborates whose structure and degree of unsaturation is conventionally described as "closo-," "nido-," "arachno-," and "hypho-" structures. These terms relate to the structure of the compounds labeled as such, meaning "cage", "nest", "web", and "net", respectively, and are understood in the art.

More preferably, the anions and radicals of this invention are of the closo-type with molecular formulas as defined in Table 1. Closo-type anions of this invention are oxidized, by a one electron oxidation, to structurally analogous radicals and radical anions. These radicals are believed to be the first known representative of odd-electron hemicloso-type polyhedral boranyls and carboranyls which are hereafter designated hemicloso species.

This invention also provides a method for making the hydrocarbon and halogenated-hydrocarbon substituted borate and carborate anions and their corresponding radicals, and derivatives thereof. A method is provided for substituting closo-borate anions and closo-carborate anions, and for oxidizing these anions to the corresponding radicals.

More specifically, a method is provided for adding hydrocarbon and halogenated- hydrocarbon substitutents to the vertices of polyhedral borate and carborate anions which may contain hydrogens or halogens. In the case of carborate anions, this can be accomplished by using the procedure reported in the literature which involves contacting the unsubstituted parent polyhedral anion with a strong base, to deprotonate the carbon vertex. The deprotonated compound is then contacted with an alkylating agent, to yield the mono-substituted compound in which the carbon has been substituted. The mono- substituted compound can then be further substituted via the method of this invention with the same or different hydrocarbon or halogenated-hydrocarbon substituent or with a halogen. In one embodiment, the substitution can be effected by halogenation of some of the vertices. If exchange of the halogens for hydrocarbon or halogenated-hydrocarbon substituents is desired, this can be accomplished by substitution at those vertices via alkyl coupling reagents. Substitution of the remaining unsubstituted vertices can be effected using a strong alkylating agent, e.g. a substituted triflate reagent. Strong alkylating agents include haloalkylating agents and therefore include akyl triflates and haloalkyltriflates.

In the case of the borate anions, the first step is omitted because there is no carbon to deprotonate and substitute. The vertices of borate anions are substituted in the same manner in which the boron vertices of carborate anions are substituted. That is, they can be halogenated and/or further substituted via strong alkylating agents.

In a preferred embodiment of the method of this invention, the mono-substituted carborate anion (substituted at the carbon) can be substituted directly by contacting it with a strong alkylating agent, for example a substituted triflate reagent; and a means to remove acid, if any acid is generated from said alkylating agent, such as a sterically hindered base or a reducing agent, such as an active metal. If a strong alkylating agent which does not generate acid, such as a diazoalkane, is used, then a means to remove acid is not needed.

When substituting carborate anions, the order of the alkylation steps can be reversed, i.e. the carbon can be deprotonated and alkylated either before or after the boron vertices are substituted.

The particular substituents added to the polyhedral borate and carborate anions and the degree of substitution can be determined by routine choice of reaction conditions by those of ordinary skill in the art.

Substituted hemicloso-boranyl and hemicloso-carboranyl radicals are made by one electron oxidation of the corresponding parent closo-anion. This oxidation can be accomplished either chemically or electrochemically.

The substituted anions and radicals of this invention can be used to form oligomers and polymers. Such polymers combine the advantages of favorable mechanical and processing properties with a high density of anions.

The anions and radicals of this invention can also form ionic complexes with metals. The metals can be main group metals, transition metals, lanthanides, or actinides. These complexes can be used in various applications, including but not limited to, as catalysts for Ziegler-Natta type polymerization reactions.

The hydrocarbon-substituted anions of this invention have a firmly bound, delocalized negative charge protected by a sheath of hydrocarbon groups. Many salts of these anions are soluble in non-polar solvents, are resistant to oxidation, and are exceptionally weakly nucleophilic. Preferably they contain no basic coordination sites such as exposed lone pairs of electrons, aromatic rings, multiple bonds or hydridic hydrogens. The hydrocarbon-substituted anions of this invention which contain multiple bonds are precursors to weakly nucleophilic compounds, polymers and oligomers. The anions substituted with halogenated-hydrocarbon substituents are more resistant to oxidation and are particularly useful for applications benefiting from such resistance to oxidation. The applications of the substituted anions which are further derivatized with various organic functionalities depend on the nature of the substituents and derivatives thereof, and in general are useful for the preparation of polymers, especially highly branched polymers. In general, the anions of this invention present the seemingly incompatible properties of being simultaneously ionic, very weakly nucleophilic and highly hydrophobic. The anionic compounds of the invention are generally useful for applications where the combination of ionic character and weak-nucleophilicity are advantageous. These include, for example, the use of salts of the compounds in non-polar solvents as catalysts for pericyclic reactions such as Diels-Alder reactions; as electrolytes in lithium batteries; as photochemical acid generators, e.g. in photoresists, based on their transparency to ultra-violet light; as counter-ions for Ziegler-Natta type polymerization catalysts; as counter-ions for extracting ions of metals, such as cesium, from radioactive waste. Because the anions can be oxidized to the corresponding radicals with an accompanying change in color, these compounds can be used as electrochromic materials, applications of which include among others displays and optical shutters. The radicals of this invention are useful as powerful oxidizing agents.

DETAILED DESCRIPTION OF THE INVENTION

Despite the need for weakly-nucleophilic anions and the existence of the known 1- carba-closo-dodecaborates, the synthesis of fully hydrocarbon-substituted 1-carba-closo-dodecaborates or any other fully hydrocarbon-substituted borate or carborate anions has not been achieved heretofore. Even the synthesis of multiply hydrocarbon-substituted borate or carborate anions has not been achieved heretofore. By providing a method for synthesizing such derivatives, the present invention now makes possible a great variety of weakly nucleophilic, anionic compounds having solubility in non-polar solvents. By varying the type and number of hydrocarbon substituents on the deltahedral structure, the volume of the anion and its affinity for various solvents and cations can be modulated. The anionic compounds of this invention can be made to undergo one-electron oxidation to their corresponding neutral radicals and radical anions. Doubly charged polyhedral borate anions can be oxidized to the corresponding radical anions.

The hemicloso-boranyl radicals have a charge of 1− and are therefore radical anions, but are referred to herein also as "radicals." The hemicloso-carboranyl radicals are neutral. It is generally appreciated in the art that anions and radical species may be very reactive and therefore unstable with relatively short lifetimes. But it is also generally appreciated that even species with relatively short lifetimes may have limited applications. Preferred radicals and anions of this invention are persistent or substantially stable. The term "substantially stable," as applied to the radicals and anions herein, means they can be isolated and stored indefinitely and have a negligible tendency to dimerize. Those of ordinary skill in the art recognize that fully hydrocarbon substituted radicals and fully halogenated-hydrocarbon substituted radicals will have the most steric protection and hence stability, but that the stability conferred by substituents depends on the exact identity/nature of the substituents and other parameters, e.g. deltahedral structure of the compound.

Most generally, the closed-shell compounds of this invention are polyhedral, including closed-shell borate anions and carborate anions whose structures are conventionally described as "closo-," "nido," "arachno-," and "hypho-" structures, as well as boranyl and carboranyl radicals which can be described as "hemicloso," "heminido," "hemiarachno," and "hemihypho." The etymology of these terms relates to the structure of the compounds labeled as such. However, no intention is made herein to limit the meaning of these terms by the structure they supposedly represent. As those skilled in the art recognize, these terms are more appropriately defined as a function of the number of skeletal electron pairs and empirical formula (Olah, G. A. et al. (1991) *Electron Deficient Boron and Carbon*, New York: John Wiley & Sons).

Anions of this invention specifically include closo-borate anions of the formula $B_nH_{(n-x)}R_x^{2-}$ wherein n is an integer from 6 to 14 and x is an integer from 2 to n, and wherein each R, independent of each other R, is a hydrocarbon substituent or halogenated-hydrocarbon substituent or a halogen; and closo-carborate anions of the formula $CB_nH_{(n+1)-x}R_x^{1-}$ wherein n is an integer from 5 to 13 and x is an integer from 2 to n+1, and wherein each R, independent of each other R, is a hydrocarbon substituent or halogenated-hydrocarbon substituent or a halogen.

Radicals of this invention specifically include hemicloso-boranyl radicals of the formula $B_nH_{(n-x)}R_x^{\bullet 1-}$ wherein n is an integer from 6 to 14 and x is an integer from 2 to n, and wherein each R, independent of each other R, is a hydrocarbon substituent or halogenated-hydrocarbon substituent or a halogen; and hemicloso-carboranyl radicals of the formula $CB_nH_{(n+1)-x}R_x^{\bullet}$ wherein n is an integer from 5 to 13 and x is an integer from 2 to n+1, and wherein each R, independent of each other R, is a hydrocarbon substituent or halogenated-hydrocarbon substituent or a halogen.

The compounds of this invention are those with 6 to 14 vertices, i.e. n is from 5 to 13 in the case of the carboranyl radicals and carborate anions, and n is 6 to 14 in the case of the boranyl radicals and borate anions. The preferred carboranyl radicals and carborate anions of this invention are those in which n is 11, i.e. those with 12 vertices. The preferred boranyl radicals and borate anions of this invention are those in which n is 12, i.e. those with 12 vertices.

"Hydrocarbon substituent," as used herein, means any linear alkyl, branched alkyl, linear alkenyl, branched alkenyl, linear alkynyl, branched alkynyl, wherein there can be any combination of one or more double bonds or triple bonds.

"Halogenated-hydrocarbon substituent," as used herein, means any halogenated- linear alkyl, halogenated-branched alkyl, halogenated-linear alkenyl, halogenated-branched alkenyl, halogenated-linear alkynyl, halogenated-branched alkynyl, wherein there can be any combination of one or more double bonds or triple bonds. Halogenated hydrocarbon substituents specifically include perhalogenated hydrocarbons, particularly perfluorinated hydrocarbons.

Halogen substituents can be added to any of the vertices of the deltahedral structures. The preferred halogen is fluorine.

Hydrocarbon and halogenated-hydrocarbon substituents of this invention can be derivatized with a variety of organic functional groups by techniques well known in the art. Derivative functional groups include, but are not limited to: amine, cyano, hydroxyl, thiol, carbonyl, carboxylate or carboxylic acid, epoxide, ester, amide, ether.

In the compounds of this invention, at least two of the vertices of each deltahedral structure are substituted with a hydrocarbon substituent or halogenated-hydrocarbon substituent, that is, a substituent other than hydrogen. The substituents on any given anion or radical can be the same or different alkyl, alkenyl or alkynyl groups, halogenated or not. The substituents on any given anion or radical can include groups of different carbon chain lengths and different numbers of double or triple bonds. Substituents that are alkenyl groups can contain one, two or more double bonds, two or more of which can be alternating double bonds (e.g., as in $CH_3-CH_2=_{CH-CH=CH2}$—). The double bonds can be cis or trans including, among others, all-cis or all-trans alkenes. The double bonds can be positioned anywhere along the length of the group, including, among others, in the ω-position (omega position). Substituents that are alkynyl groups can contain one, two or more triple bonds positioned anywhere along the length of the group. Both double and triple bonds can be present in any given substituent.

Substituents may be longer chain species containing more than about 7 carbon atoms or shorter chain species containing one to about 6 carbon atoms. Compounds of this invention include, among others, those compounds in which the substituents have from one to about 20 carbon atoms and those which have from one to about 6 carbon atoms. Hydrocarbon substituents can be selected from methyl, ethyl, n-propyl, n-butyl, n-pentyl, n-hexyl, iso-propyl, sec-butyl, t-butyl, ethenyl, propenyl, butenyl, pentenyl, hexenyl, acetylenyl, propynyl, butynyl, pentynyl or hexynyl groups. Representative alkyl groups also include among others n-heptyl, n-octyl, n-nonyl, n-decyl, n-undecyl, and n- dodecyl groups. More preferred hydrocarbon substituents include methyl, ethyl and n- propyl. Methyl is the most preferred hydrocarbon substituent.

Halogenated-hydrocarbon substituents include, among others, those which have from one to about 20 carbon atoms, including longer chain species with 7 or more carbon atoms and shorter chain species which have from one to about 6 carbon atoms. Halogenated-hydrocarbon substituents can have any degree of halogenation, i.e. the substituent may have one or more halogens. Specifically, the substituent can be perhalogenated. Halogenated-hydrocarbon substituents can be selected from trihalomethyl goups, particularly trifluoromethyl and partially halogenated species such as 2,2, 2,-trihaloethyl groups, particularly, 2,2,2- trifluoroethyl. Trifluoromethyl is the most preferred halogenated-hydrocarbon substituent.

Compounds of this invention include, among others, those in which at least two vertices are substituted with alkyl, alkenyl or alkynyl groups, particularly with methyl or ethyl groups. Compounds of this invention also include, among others, those in which several vertices are substituted with H and the remainder of the substituents are alkyl, alkenyl or alkynyl, particularly where the remainder are methyl or ethyl groups. Those skilled in the art recognize that for any given deltahedral structure, different vertices have more or less electron density and therefore are more or less reactive with an alkylating agent. The method for synthesizing the substituted anions of this invention takes advantage of this fact, and allows for adding hydrocarbon or halogenated-hydrocarbon substituents or halogens to certain vertices while other vertices remain substituted with hydrogen, if desired. Compounds of this invention also include, among others, those in which all of R are alkyl, alkenyl or alkynyl groups, particularly those where all of R are methyl or ethyl groups and more particularly where all of R are methyls or all of R are ethyls. This invention also includes compounds where R can be selected from branched alkyl groups, including α-branched alkyl groups, having one to five carbon atoms. Where the substituents, R, include α-branched alkyls then preferred compounds are those in which not all substituents are or-branched. Compounds of this invention also include those in which the substituents are selected from alkenyls having 2 to 8 carbon atoms.

The compounds of this invention include compounds substituted with a variety of substituents, e.g. compounds in which some substituents are halogens and some are hydrocarbon and/or halogenated hydrocarbon substituents.

The anions of this invention can be isolated as salts of a variety of counter-ions (cations). The counter-ions include, among others, metal cations in general. More particularly they include cations of alkali metals and alkaline earth metals. Examplary counter-ions include, among others, lithium ion, sodium ion, potassium ion, magnesium ion, calcium ion, ammonium ion, silver ion, tetraphenylphosphonium ion, dimethylanilinium ion, trimethylammonium ion, tetramethylammonium ion and other tetraalkylammonium ions and $H_3O+$.

A variety of salts can be prepared by an electron transfer reaction using the carboranyl or boranyl radical as a starting material. For example, reacting said radical with triphenylamine yields the triphenylammonium salt of the corresponding anion. Other reagents which can donate an electron to the radical in this type of electron transfer reaction, including other trialkylamines, can be used. Those of ordinary skill in the art will recognize that variations of this reaction can be made by routine choice of reaction conditions and reagents.

The synthesis of the anions of this invention is exemplified by the synthesis of the fully methyl-substituted dodecaborate anion, $CB_{11}Me_{12}^{1-}$. Substitution by other hydrocarbon substituents on the dodecaborate deltahedral structure and substitution by methyl or other hydrocarbon substituents on other deltahedral structures can be readily carried out by similar reaction steps or by routine modifications or adaptations of these reactions. Partially or fully-substituted borate and carborate anions can be synthesized by employing the guidance herein with routine selection of starting materials and application of synthetic techniques well known in the art.

In a specific embodiment, the anions of this invention include those of Formula A:

Formula A
1, $R_1$–$R_{12}$ = Me (fully methylated anion)
2, $R_1$–$R_{12}$ = H (unsubstituted anion)
3, $R_1$ = Me, $R_2$–$R_{12}$ = H (mono-methylated anion)

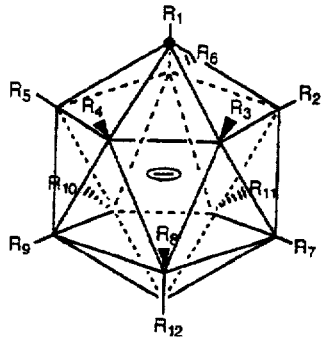

where $R_1$–$R_2$ are substituents as defined above for R and which includes the fully methylated anion 1.

Formula A is a structural diagram for the icosahedral dodecaborate anion deltahedral structure. Each vertex represents a boron atom except for position number one where the larger dot represents the single carbon atom of the carbadodecaborate anion deltahedral structure. $R_1$–$R_2$ represent substituents at positions 1–12 on the carbadodecaborate anion deltahedral structure, respectively. In the compounds of this invention, at least two of the vertices of each deltahedral structure are substituted with a hydrocarbon substituent, that is, a substituent other than hydrogen.

Compounds of Formula A include, among others, those in which no more than 10 of $R_1$–$R_{12}$ are H and the remainder of $R_1$–$R_{12}$ are alkyl, alkenyl or alkynyl groups or halogen, particularly where the remainder are methyl or ethyl groups and more particularly where $R_1$ and $R_{12}$ are methyl or ethyl groups. Compounds of Formula A also include, among others, those in which 5 of $R_1$–$R_{12}$ are H and the remainder of $R_1$–$R_{12}$ are alkyl, alkenyl or alkynyl, particularly where the remainder are methyl or ethyl groups and more particularly where $R_1$, and $R_7$–$R_{12}$ are methyl or ethyl groups. Compounds of Formula A also include, among others, those in which all of $R_1$–$R_{12}$ are alkyl, alkenyl or alkynyl groups, particularly those where $R_1$–$R_{12}$ are methyl or ethyl groups and more particularly where all of $R_1$–$R_{12}$ are methyls or all of $R_1$–$R_{12}$ are ethyls. Compounds of Formula A also include, among others, those in which all of $R_1$–$R_{12}$ are halogenated-alkyl, -alkenyl or -alkynyl groups, particularly those where $R_1$–$R_2$ are trifluoromethyl or 2,2,2-trifluoroethyl groups and more particularly where all of $R_1$–$R_2$ are trifluoromethyl or all of $R_1$–$R_{12}$ are 2,2,2-trifluoroethyl groups. Compounds of Formula A include compounds with a variety of substituents, e.g. compounds in which some substituents are halogens and some are hydrocarbon and/or halogenated hydrocarbon substituents.

The ions of Formula A can be precipitated as salts of a variety of counter ions (cations). The counter-ions include, among others, quaternary ammonium ions and metals in general. More particularly they include alkali metals and alkaline earth metals. Exemplary counter-ions include, among others, lithium ion, sodium ion, potassium ion, magnesium ion, calcium ion, ammonium ion, silver ion, tetraphenylphosphonium ion, dimethylanilinium ion, trimethylammonium ion, tetramethylammonium ion and other tetraalkylammonium ions and $H_3O^+$.

The synthesis of the radicals of this invention is exemplified by the synthesis of the fully methyl-substituted monocarba-hemicloso-dodecaboranyl radical, $CB_{11}Me_2^*$. Substitution by other hydrocarbon substituents on the dodecaboranyl radical deltahedral structure and substitution by methyl or other hydrocarbon substituents on other deltahedral structures can be readily carried out by similar reaction steps or by routine modifications or adaptations of these reactions. Partially or fully substituted boranyl and carboranyl radicals can be synthesized by employing the guidance herein with routine selection of starting materials and application of synthetic techniques well known in the art.

In a specific embodiment, the radicals of this invention include those of Formula B:

Formula B
1', $R_1$–$R_{12}$ = Me (fully methylated radical)
2', $R_1$–$R_{12}$ = H (unsubstituted radical)
3', $R_1$ = Me, $R_2$–$R_{12}$ = H (mono-methylated radical)

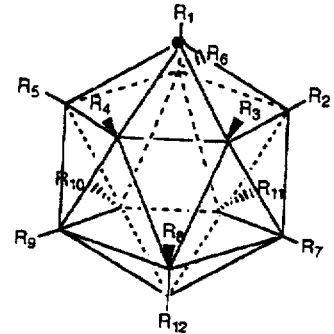

where the substituents $R_1$–$R_{12}$ are defined as for anions of Formula A.

Like Formula A, Formula B is a structural diagram for the icosahedral dodecaboranyl radical deltahedral structure. Each vertex represents a boron atom except for position number one where the larger dot represents the single carbon atom of the carbadodecaboranyl radical deltahedral structure. $R_1$–$R_{12}$ represent substituents at positions 1–12 on the carbadodecaboranyl radical deltahedral structure, respectively. In compounds of Formula B of this invention, at least two of the vertices of each deltahedral structure are substituted with a hydrocarbon substituent, that is, a substituent other than hydrogen.

Compounds of Formula B include, among others, those in which no more than 10 of $R_1$–$R_{12}$ are H and the remainder of $R_1$–$R_{12}$ are alkyl, alkenyl or alkynyl groups or halogens, particularly where the remainder are methyl or ethyl groups and more particularly where $R_1$ and $R_{12}$ are methyl or ethyl groups. Compounds of Formula B also include, among others, those in which 5 of $R_1$–$R_{12}$ are H and the remainder of $R_1$–$R_{12}$ are alkyl, alkenyl or alkynyl, particularly where the remainder are methyl or ethyl groups and more particularly where $R_1$, and $R_7$—$R_{12}$ are methyl or ethyl groups. Compounds of Formula B also include, among others, those in which all of $R_1$–$R_{12}$ are alkyl, alkenyl or alkynyl groups, particularly those where $R_1$–$R_{12}$ are methyl or ethyl groups and more particularly where all of $R_1$–$R_{12}$ are methyls or all of $R_1$–$R_{12}$ are ethyls. Compounds of Formula B also include, among others, those in which all of $R_1$–$R_{12}$ are halogenated-alkyl, -alkenyl or -alkynyl groups, particularly those where $R_1$–$R_{12}$ are trifluoromethyl or 2,2,2-trifluoroethyl groups and more particularly where all of $R_1$–$R_{12}$ are trifluoromethyl or all of $R_1$–$R_{12}$ are 2,2,2-trifluoroethyl groups.

In general, the substitution of the carborate anions is accomplished by the following method, the first step of which, C-alkylation, has been reported in the literature. In the first step, the anion is deprotonated and then substituted at the carbon. A salt of the anion is contacted with a strong base in an inert solvent. A "strong base," as used herein, means any base strong enough to deprotonate the carbon of the carborate anion. Examples of strong base include, but are not limited to, any alkyllithium, e.g. butyllithium; Grignard reagents, e.g. ethylmagnesium bromide; lithium diisopropylamide (LDA); bis-trimethylsilylamide; other organometallic compounds. The deprotonated compound is then substituted at the carbon vertex, by contacting the compound with an alkylating reagent. An "alkylating reagent," as used herein with regard to preparing the mono-substituted carborate anion by means already reported in the literature, means a compound capable of transferring to the carbon of the anion an alkyl or other hydrocarbon substituent. Examples of alkylating reagents include, but are not limited to, alkyl halides, benzyl halides, alkenyl halides, alkynyl halides, allylic halides, sulfonate esters. Examples of alkyl halides include, but are not limited to, methyl iodide, ethyl iodide, methyl bromide. Examples of sulfonate esters include, but are not limited to, ethyl mesylate, methyl tosylate and methyl triflate. The product formed is a mono-substituted anion, that is an anion with one hydrocarbon substituent bound to it.

The mono-substituted (C-alkylated) carborate anion is then further substituted with hydrocarbon and/or halogenated-hydrocarbon substituents or halogens. In one embodiment of the reaction (see Examples 1–9), further substitution is accomplished in several steps. The subsequent substitutions can be made by first halogenating the mono- substituted anion. Halogenation can be accomplished by contacting the mono-substituted anion with a halogenating reagent, for instance molecular iodine ($I_2$), or iodine monochloride ($IC_1$). Contacting this mono-substituted, (partially) halogenated anion with an alkyl coupling reagent with a palladium-based catalyst effects the exchange of the halogens for hydrocarbon substituents. Contacting this partially-hydrocarbon-substituted anion with a substituted triflate effects the complete substitution of the anion.

In a preferred embodiment of the reaction the mono-substituted carborate anion is fully substituted in one step by contacting it with a strong alkylating agent; and optionally, a means to remove acid, if any acid is generated. Strong alkylating agents includes substituted trifluoromethane sulfonate (triflate), methyl fluorosulfate, and diazoalkane. Strong alkylating agents do not include alkyl halides, which are used in the method reported in the literature (Jelinek, T. et al. (1993) *Inorg. Chem.* 32: 1982) and which are used to prepared the mono-alkylated anions. A means to remove acid can include, but is not limited to, any sterically hindered base or other bases which do not react with the alkylating agent, such as a hydride; or a reducing agent, such as an active metal. In general, the borate anions are substituted in the same manner in which the mono-substituted carborate anions are substituted. The borate anions are substituted by contacting them with a strong alkylating agent and optionally, a means to remove acid, if any acid is generated.

A means to remove acid is also a means to capture a nucleophilic leaving group and is necessary if the leaving group of the strong alkylating agent is nucleophilic, e.g. as triflate is. A means to remove acid inhibits the nucleophilicity of the leaving group, thereby preventing the nucleophilic leaving group from attacking the anion. A sterically hindered base, e.g. di-t-butylpyridine or any substituted di-t-butylpyridine, captures the nucleophilic leaving group. Other bases which are not nucleophilic, such as hydrides, can also be used. Another means of removing acid (and thereby inhibiting the nucleophilicity of the leaving group of a strong alkylating agent) is by using a reducing agent such as an active metal, e.g. magnesium. An active metal will reduce the acidic proton to hydrogen gas and coordinate with the nucleophilic leaving group.

An alternative to using a strong alkylating agent which generates acid because it has a nucleophilic leaving group is to use a strong alkylating agent which does not generate acid. Diazoalkanes, among other known strong alkylating agents, do not have nucleophilic leaving group and therefore do not generate acid. Thus, a means to remove acid is unnecessary. Diazomethane is the preferred diazoalkane.

The use of excess strong alkylating agent for a sufficient time generally leads to full or per-substitution. The degree of substitution accomplished can be decreased by using lower amounts of strong alkylating agent, e.g. less than one mole equivalent compared to the anion starting material being substituted. A mixture of products of varying degrees of substitution, e.g. mixtures of products with 2, 3, 4, 5 and so on of the vertices substituted, may be formed depending on the reaction conditions. If less than full-substitution is desired, reducing the mount of strong alkylating agent, reducing the temperature of the reaction, stopping the reaction after a shorter reaction time before persubstitution occurs and/or other modifications which can be made without undue experimentation will lead to partial substitution, as will be recognized by those of ordinary skill in the art.

It will be recognized by those in the art that when two or more different substituents are to be added to the deltahedral structures, it may be preferable to perform a partial substitution with the bulkier substituent(s) first, followed by substitution with the smaller substituent(s). It will also be recognized that certain positions may be more readily substituted with certain substituents. For example, in the dodecaborate anion, the 12-position may be preferred for halogen substitution. It will further be recognized that the stability of the substituted anions may be affected by the nature/identity of the substituents. For example, halogen substituents at the vertices of carborate and borate anions may increase the stability of the anions, because the halogens make the anion harder to oxidize.

The use of substituted triflate as a strong alkylating agent is preferred. "Substituted triflate," as used herein, means a triflate group ($CF_3SO_3$—) covalently bound at the sulfonate oxygen to a hydrocarbon group. Examples of substituted triflates include, but are not limited to, methyl triflate, ethyl triflate, trifluoromethyl triflate, and 2,2,2-trifluoroethyl triflate. Substituted triflates are prepared from appropriate alcohols and trifluoromethylsulfonyl chloride.

"A means to remove acid" includes, among others, a sterically hindered base and reducing agents. We believe that the concentration of acid in the reaction solution must be minimized because acid leads to unwanted side-reactions. We believe that acid leads to formation of unwanted by-products and to the destruction of the starting material (anion), the partially substituted anions and the fully substituted anions. "A sterically hindered base," as used herein, means a base which can promote the substitution of the anion but has sufficiently low Lewis base character that it doesn't react with the alkylating agent or promote unwanted side-reactions. We believe that the sterically hindered base reacts with acid which is produced during the reaction, thereby reducing the concentration of acid. Examples of sterically hindered bases include, but are not limited to, 2,6-di-t-butylpyridine; other substituted -di-t-butylpyridine derivatives; and "proton sponge" which is N,N,N',N'-tetramethyl-1,8-naphthalenediamine (*Chem. Commun.* (1968) 723). Other bases which do not react with the alkylating agent and are useful in the present methods include hydrides, such calcium hydride and sodium hydride. Another means of removing acid is a reducing agent. For example magnesium metal can be added to the reaction solution, wherein magnesium reacts with acid, yielding hydrogen gas and oxidized magnesium in the form of magnesium triflate.

A dehydrating reagent is not required for synthesizing the anions of this invention, but including one in the reaction mixture can lead to improved product yield in some cases. A "dehydrating reagent," as used herein, means a chemically inert compound capable of removing trace quantities of water. Examples of dehydrating reagents include, but are not limited to, lithium hydride, calcium hydride, molecular sieves and magnesium sulfate.

In general, one embodiment of the synthesis of dodecamethyl-1-carba-closo-dodecaborate (−) anion is described, with experimental details in the specific examples. Starting with the $Me_3NH^+$ salt of the long-known (Knoth, W. H. (1967) *J. Am. Chem. Soc.* 89:1274; Plesek, J., et at. (1984) *Coll. Czechoslov. Chem. Comm.* 49:1559) 1-carba-closo-dodecaborate (−) anion ($R_{-12}$=H) 2, the twelve methyl substituents were introduced sequentially in groups of one, six, and five. The C-Li salt of 2 was alkylated with MeI (in analogy to Jelinek, T. et al. (1993) *Inorg. Chem.* 32:1982) affording the 1-methyl derivative ($R_1$=methyl) 3. The presence of the 1-methyl group facilitated an iodination with $I_2$ to the 12-substituted monoiodide 4 ($R_1$=methyl, $R_{12}$=I), and subsequently with IC1, which introduced five additional iodine atoms into positions 7–11 to yield the hexaiodide 5 ($R_1$=methyl, $R_{7-12}$=I). The six iodine substituents were then exchanged for six methyls in a Pd-catalyzed coupling reaction with MeMgI (Zakharkin, L. I. et at. (1982) *J. Organomet. Chem.* 226:217; Ji Li, et at. (1991) *Inorg. Chem.* 30:4866), yielding the heptamethylated anion 6 ($R_{1,7-12}$=methyl). Although this readily underwent pentaiodination with IC1, the resulting pentaiodoheptamethyl anion 7 ($R_{1,7-12}$=methyl, $R_{2-6}$=I) was not useful in that it reacted only incompletely with MeMgI in the presence of a Pd catalyst, possibly due to excessive steric hindrance. However, direct pentamethylation of 6 with methyl triflate was successful and afforded the desired dodecamethyl anion 1 ($R_{1-12}$=methyl). Direct permethylation of $(CB_{11}H_{12})NH(CH_3)_3$ 2, $(1—CH_3—CB_{11}H_{11})N(CH_3)_4$ 3 and $[1,12—(CH_3)_2—CB_{11}H_{10}]N(CH_3)_4$ 9 with methyl triflate also be carried out.

In a preferred embodiment of the reaction, substitution can be accomplished in one step by starting with the mono-substituted (C-alkylated) anion. The synthesis of dodecamethyl-1-carba-closo-dodecaborate(-) anion is provided as a specifically lo exemplified embodiment of this method. Synthesis of the other anions of this invention can be accomplished by routine selection of starting materials and application of synthetic techniques known to those skilled in the art.

In the preferred embodiment, trimethylammonium carba-closo-dodecaborate (−) (2, $CB_{11}$, $H_{12}^-$) was methylated on carbon in 87% yield using the known literature procedure for C-alkylation (in analogy to Jelinek, T. et al. (1993) *Inorg.*

*Chem.* 32: 1982). The $(CH_3)_4N^+$ salt of the resulting 1-methylcarba-closo-dodecaborate(-) anion (3, $MeCB_{11}H_{11}^-$) was permethylated with excess methyl triflate in the presence of 2,6-di-t-butylpyridine and $CaH_2$, then converted to a $Ph_4P^+$ salt of 1 $(CB_{11}Me_{12}^{1-})$, by ion exchange (after crystallization from MeOH). The purity of the product was greater than 95% and the yield was 48%. See Example 10 for details of this reaction.

Salts of 1 appear to be very stable to air, bases (several days in KOH/EtOH), and dilute acids (overnight in 5 % $H_2SO_4/Et_2O$), but are destroyed after several hours in concentrated $H_2SO_4$ or $CF_3SO_3H$. Both the hydrated and anhydrous $Li^+$ salts of 1 are very soluble in polar solvents, including chloroform, and fairly soluble in carbon tetrachloride and toluene.

Multiply substituted polyhedral anions and radicals of this invention can be derivatized and thereby contain one or more organic functionalities including, but not limited to, amine, cyano, hydroxyl, thiol, carbonyl, carboxylate or carboxylic acid, epoxide, ester, amide, ether, or any other common organic functional group. These functionalities may be present on the substituted triflate or other alkylating agent or these functionalities may be added to the hydrocarbon substituent after it has been added to the anion using synthetic techniques known to those of ordinary skill in the art.

As will be understood by those of ordinary skill in the art, the degree of full substitution with branched hydrocarbons may be restricted by steric factors, particularly in the case of alpha-branched hydrocarbon groups, given the volumes occupied by such groups. Where branching occurs more distal to the deltahedral structure, more space is available to accommodate more branched substituents, as can be understood from the geometry of the molecule. Substitution of the anion by one or more alkenyls or other polymerizable derivatives makes it possible to form polymers of the anion, either linear or branched, depending upon the number of substituents and conditions of polymerization. Polymerization can also take place in the presence of co-monomers to form a variety of polyanions whose anionic character and spacing between the anions can be varied depending on the proportions of anion and co-monomer. Opportunities for other variations including, without limitation, synthesis of branched polymers, copolymers and block copolymers, will be readily appreciated by those skilled in the art as lying within the scope of the invention.

One electron oxidation of the anions of this invention yields the corresponding radicals. In the case of the borate anions of this invention, the corresponding radicals resulting from one-electron oxidation have a 1− charge. In the case of the carborate anions of this invention, the corresponding radicals resulting from one-electron oxidation are neutral. Because of the steric protection afforded by the substituents, these radicals are generally stable.

The oxidation of the anions to the corresponding radicals can be accomplished by chemical and electrochemical means. The following examples illustrate the synthesis of the radicals of this invention. Other radicals of this invention can be readily synthesized by routine modifications or adaptations of this reaction and by employing the guidance herein with routine selection of starting materials and application of synthetic techniques well known in the art.

The anions of this invention can be oxidized to their corresponding free radicals chemically by the use of a strong oxidizing agent. "Strong oxidizing agent," as used herein, means an oxidizing agent strong enough (with a high enough oxidation-reduction potential) to oxidize the anions of this invention. A solvent compatible with chosen oxidizing agent and starting materials must be used, as many oxidizing agents are formed in situ by reaction of the solvent with another compound. For instance, $PbO_2$ reacts with acetic acid or trifluoroacetic acid to form the reactive oxidizing agent, lead tetraacetate or lead tetratrifluoroacetate, respectively. The choice of appropriate solvent can be made by those of ordinary skill in the art.

The cesium salt of dodecamethylcarba-closo-dedecaborate(−) 1 was oxidized to the neutral free radical chemically with $PbO_2/CF_3COOH$ in up to quantitative yield and also electrochemically in acetonitrile. Details of the chemical oxidation follow.

To a 10 mL solvent system of $MeCN/CF_3COOH$ (9/1), $PbO_2$ (280 mg) and $Cs^+(CH_3)_{12}CB_{11}^{1-}$ (32 mg, note that the anion is white) were added. Pentane (10 mL) was added and the reaction mixture was stirred vigorously for 3 minutes. The blue top layer was collected, then extracted a second time with pentane. (The blue color is an indicator of the presence of the radical.) The combined pentane layers were washed with 5% NaOH (aq) then dried over $MgSO_4$. Solvent was removed at 0° with a stream of Ar in the absence of light, giving a blue-black residue (12 mg, 54%).

The cesium salt of dodecamethylcarba-closo-dedecaborate(−) 1 can also be oxidized to the neutral free radical electrochemically. A conventional electrochemical cell, which is a container equipped with an anode, a cathode, a reference electrode and a salt bridge, is used. An inert solvent, e.g. methylene chloride, is used to dissolve the salts of the anions. Platinum electrodes and tetrabutylammonium hexafluorophosphate as the electrolyte for the salt bridge were used to oxidize dodecamethylcarba-closo-dedecaborate anion to the neutral radical.

The $(CH_3)_{12}CB_{11}$ neutral radical forms shiny black tetrahedrally shaped crystals stable in air in daylight, and dissolves in non-polar solvents, e.g. pentane and diethyl ether, to give deep blue solutions, stable to air, UV and visible irradiation. It is destroyed by heating above 160° C. We believe the stability of the $(CH_3)_{12}CB_{11}$ neutral radical is attributable to steric protection of the delocalized free valence carrying centers in the carborate anion icosahedron by the sheath of methyl substituents, which is apparently effective against even relatively small molecules such as oxygen.

The cathodic reduction potential of the $(CH_3)_{12}CB_{11}$ neutral radical in acetonitrile is 1.6 V ($Bu_4NF$, Ag/AgCl; ferrocene, 0.45 V), equal to the anodic oxidation potential of the $(CH_3)_{12}CB_{11}^{1-}$ anion. Reducing agents destroy the blue color of solutions of the $(CH_3)_{12}CB_{11}$ neutral radical and convert the radical to the $(CH_3)_{12}CB_{11}^{1-}$ anion. Unlike many common one-electron oxidants and/or their reduced forms, both the $(CH_3)_{12}CB_{11}$ neutral radical and the $(CH_3)_{12}CB_{11}$ anion are quite lipophilic, and the conversion of one into the other is homogeneous even in solvents as non-polar as toluene.

The anions, including the radical anions, of this invention can also form ionic complexes with metals. The metals can be main group metals, transition metals, lanthanides, or actinides. "Ionic complexes with metals," as used herein, means an aggregation of one or more molecules of the compounds of this invention with one or more metal atoms, which may or may not be bound to other ligands. Metals and chelated metals which can form complexes with the compounds of this invention include, but are not limited to, Fe, Ru, Ag, Cs, Zr and Os. For example, zirconium can form many complexes with the anions of this invention. Zirconocene and iron-porphyrins also form ionic complexes with the anions of this invention. The aggregation is held together by ionic bonds between the metal and the compounds of this invention. Ionic complexes with metals include, but are not limited to, complexes with two anions bound to one metal atom. Ionic complexes with metals include monomeric triple-deckers, linked double- and triple-decker sandwich complexes, and oligomeric and polymeric triple-deckers. (Olah, G. A. et al. (1991) *Electron Deficient Boron and Carbon*, New York: John Wiley & Sons) These complexes can be used in various applications, including but not limited to, applications as catalysts for Ziegler-Natta type polymerization reactions.

The compounds of this invention can be applied in many ways including, but not limited to, batteries and electrochromic displays. The properties of the compounds of this invention can be chosen by the identity of substituents and degree of substitution on any given deltahedral structure. For example, the redox potential of the compounds of this invention can be modified by the identity/nature of the substituents added and by the number of substituents added. In the case of the $(CH_3)_{12}CB_{11}$ neutral radical / $(CH_3)_{12}CB_{11}^{1-}$ anion system, for instance, the oxidation-reduction potential can be modified by reducing the number of electron-donating methyl groups and by choosing different substituents to add to the deltahedral structure. As noted in the discussion above regarding the first embodiment of the synthesis of the substituted anions, the heptamethylated anion $(CH_3)_7CB_{11}H_5^{1-}$ was formed in the course of synthesizing the fully-methylated anion. And in the preferred embodiment, partial substitution can be accomplished by routine choices of reaction conditions capable of those of ordinary skill in the art. In the case of the $(CH_3)_{12}CB_{11}$ neutral radical / $(CH_3)_{12}CB_{11}^{1-}$ anion system, for instance, the oxidation potential can be increased well beyond 2.5 V, the minimal value estimated for the unsubstituted $CB_{11}H_{12}^{1-}$ anion by adding $CF_3$-substituents instead of $CH_3$-substituents. A $(CF_3)_{12}CB_{11}$ neutral radical / $(CF_3)_{12}CB_{11}^{1-}$ anion system can be used to make an unusually high voltage battery.

Among others, the $Li^+$ salts of the anions of this invention are solid-state conductors and therefore useful in a battery or an electrochromic system.

An example of a solid battery configuration is a layered structure of $Pt//Li^+CB_{11}Me_{12}^{1-}//Li^+CB_{11}H_5Me_7^{1-}//Li$. The salt may be incorporated in a polymer layer. Charging will pump holes into $CB_{11}Me_{12}^{1-}$ and gradually convert it into $CB_{11}Me_{12}^{\bullet}$. The holes cannot pass through $CB_{11}H_5Me_7^{1-}$ because of its higher oxidation potential. The Li+ cation travels without excessive resistance through $CB_{11}Me_{12}^{1-}$ as well as $CB_{11}H_5Me_7^{1-}$ and accepts electrons at the Li electrode to form more Li metal.

Because of the electrochromic nature of the compounds of this invention, these compounds can be used in electrochromic devices, such as electrochromic displays. Slow display applications, including signs, are among those provided by the compounds of this invention. Other electrochromic applications include windows and plane canopies.

An example of an electrochromic configuration is a layered structure of conducting glass//$Li^+CB_{11}Me_{12}^{1-}$//$Li^+CB_{11}H_5Me_7^{1-}$//$WO_3$//conducting glass. Because the anion is colorless and the radical (solid) is black, this system is colorless before the passage of current and black after the passage of current. In this system the compounds can be neat solids, deposited on the glass by sublimation. Additionally, solutions of the compounds in various polymers, including polyethers and hydrocarbon polymers such as polystyrene, can be utilized.

Hydrocarbon polymers have advantages over polyethers for electrochromic applications because the binding of $Li^+$ to the ether oxygens is quite strong and its binding to hydrocarbons, such as the aromatic ring in polystyrene is weaker. Hence, the conductivity is expected to be higher in hydrocarbon polymers than in polyethers.

The compounds of this invention can be used to make conducting polymers, which are polymers which conduct electricity. The two types of conductive polymers discussed below are meant to illustrate some of the applications of the compounds of this invention, but are in no way intended to limit the applications of the compounds or the scope of this invention.

The polymers and oligomers of this invention can be those in which the anions and radicals are attached to a backbone or are directly attached to each other. See below for a diagrammatic representation of some the polymers of this invention.

Schematic of Possible Polymers

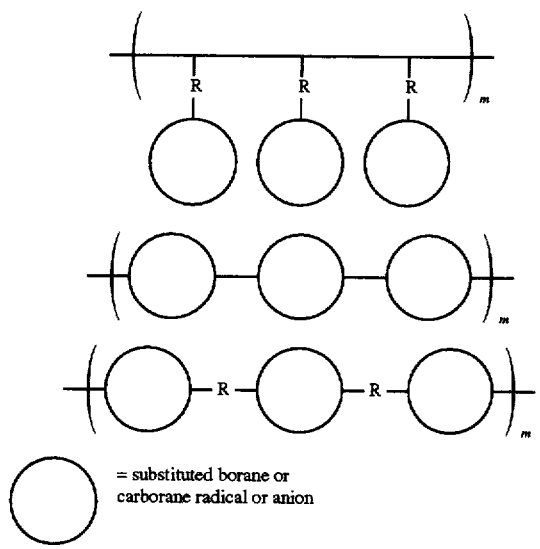

◯ = substituted borane or carborane radical or anion m = number of times the unit in parentheses is repeated; a large number.

One exemplary polymer contains a backbone with a higher oxidation potential than the laterally attached borate or carborate anion. The backbone can be, among others, polyalkene such as polyethylene, polypropylene, or polybutadiene. Thus, in the oxidized form, the laterally attached anion will have been oxidized to the corresponding radical. In this type of polymer, hole conduction will occur from one lateral group (radical) to another.

Another type of polymer contains a backbone with a lower oxidation potential than the laterally attached anion. The backbone can be, among others, polysilanes, polyacetylenes, or polydiacetylenes. Thus the oxidized form of this type of polymer has mobile charge-carrying holes in the polymer backbone and their positive charge will be compensated for by the inert laterally attached anions. Hence, this is a self-doped electronically conducting polymer.

EXAMPLES

Example 1

$(12\text{-}1\text{---}CB_{11}H_{11})NH(CH_3)_3$ (10) The literature procedure (Jelinek, T. et al. (1993)) was modified because the reaction ran only slowly and incompletely under the conditions reported. $(CB_{11}H_{12})NH(CH_3)_3$ (2) (Boudjouk, P. and Bahr, S. R. (1992) *J. Org. Chem.* 57:5545; Bahr, S. R. and Boudjouk, P. (1993) *J. Am. Chem. Soc.* 115:4512) (1.00 g, 4.92 mmol) was treated with 4M HCl (50 mL), and the free acid $(CB_{11}H_{12})H_3O$ was extracted to diethyl ether (4×25 mL). The ether was distilled off using a rotary evaporator and the residue was dissolved in glacial acetic acid (50 mL). 12 (1.25 g, 4.93 mmol) was added to the reaction mixture, which was then stirred at 60° C. until the signals of 2 disappeared in $^{11}B$ NMR (about 72 h). Sodium sulfate (0.3 g) was then added and solvents were distilled off on a rotary evaporator. The residue was dissolved in water (50 mL), and an aqueous solution of $(CH_3)_3N.HCl$ was used to precipitate the cluster as a trimethylammonium salt. The solid was filtered, washed with water, recrystallized from aqueous methanol, filtered again, and vacuum dried. Yield: 0.79 g (49%).

Example 2

$(12\text{---}CH_3\text{---}CB_{11}H_{11})NH(CH_3)_3$ (8) ($R_{12}$=methyl). $(12\text{-}I\text{---}CB_{11}H_{11})N(CH_3)_4$ (10, 0.87 g, 2.54 mmol) was placed in dry THF (60 mL) and cooled to -30 ° C in a nitrogen atmosphere. Then $CH_3MgI$ (2.0 mL, 3M in diethyl ether, 6.0 mmol) was added dropwise with stirring, followed immediately by $(Ph_3P)_2PdCl_2$ catalyst (80 mg, 0.11 mmol). The mixture was allowed to come to room temperature and refluxed overnight. After adding it to ice (30 g), 4M HCl (10 mL) was added, and the THF was removed on a rotary evaporator. The mixture was then extracted into diethyl ether (5×10 mL), the ether layers were combined with water (20 mL) and evaporated to transfer the compound to an aqueous solution. $(CH_3)_3N.HCl$ (0.26 g, 2.61 mmol) dissolved in a minimal mount of water was added to the solution, and the white precipitate was vacuum filtered and dried. Yield: 0.35 g (63%). The product was recrystallized from aqueous methanol.

Example 3

$[1,12\text{---}(CH_3)_2\text{---}CB_{11}H_{10}]N(CH_3)_4$ (9) ($R_{1,12}$=methyl). $(12CH_3\text{---}CB_{11}H_{11})NH(CH_3)_3$ (8, 0.17 g, 0.78 mmol) was dissolved in THF (10 mL), to which BuLi (1.25 mL, 1.6M in hexane, 2.0 mmol) was added under $N_2$ with stirring. Reaction was allowed to continue for 2 h. $CH_3I$ (0.06 mL, 1.0 mmol) was then added, and after 1/2 h, LiI precipitate was filtered. The mixture was rotary evaporated to remove THF, and dissolved in 5% NaOH (30 ml). The product was precipitated by the addition of $N(CH_3)_4BF_4$ (126 mg, 0.78 mmol) dissolved in a minimal mount of water. The solid was filtered, dried, dissolved in $CHCl_3:CH_3CN$ (3:1), and eluted with the same solvent mixture through a silica column. Fractions were rotary evaporated and dried under reduced pressure (oil pump). The residue was dissolved in 5% NaOH, reprecipitated with the aqueous solution of the tetramethylammonium salt, filtered, and dried. Yield: 0.14 g (73%).

Example 4

$(1\text{---}CH_3\text{---}CB_{11}H_{11})N(CH_3)_4$ (3) ($R_1$=methyl). $(CB_{11}H_{12})NH(CH_3)_3$ (2)[5] was dissolved in THF (20 mL) under nitrogen atmosphere. To this solution was added BuLi (4.13 mL, 1.6M in hexane, 6.6 mmol) dropwise with stirring. The reaction was allowed to nm for 2 h, at which point $CH_3I$ (0.20 mL, 3.2 mmol) was added. After half an hour, the LiI precipitate was filtered off, and the filtrate was evaporated and dried thoroughly under vacuum. The residue was dissolved in 5% NaOH (50 mL). This solution was precipitated with $N(CH_3)_4BF_4$ (0.52 g, 3.20 mmol) dissolved in a minimal amount of water. The precipitate was filtered and dried. $^{11}B$ NMR showed an approximate 1:10 mixture of starting material with product. The solid was dissolved in acetone, and of silica (5 g) was added. The mixture was evaporated and the residue was passed through a silica gel column with $CHCl_3:CH_3CN$ (3:1). Fractions containing the product were combined, dried, and the product was recrystallized. Yield: 0.64 g (92%).

Example 5

$(1-CH_3-12-I-CB_{11}H_5)N(CH_3)_4$ (4) ($R_1$=methyl, $R_{12}$=I). 3 (0.6 g, 2.60 mmol) was dissolved in acetic acid (40 mL). $I_2$ (0.75 g, 3.0 mmol) was added, and the mixture was stirred at 60° C. overnight. Sodium sulfate (0.3 g) was added and the acetic acid was rotary evaporated. The residue was dissolved in 5% NaOH (40 mL) and precipitated by the addition of $N(CH_3)_4BF_4$(0.42 g, 2.60 mmol) dissolved in a minimal mount of water. The solid was filtered and dried. Yield of crude material: 0.73 g (79%). This was further purified by chromatography on a silica gel column with $CHCl_3:CH_3CN$ (3:1).

Example 6

$(1-CH_3-7,8,9,10,11,12-I_6-CB_{11}H_5)N(CH_3)_4$ (5) ($R_1$= methyl, $R_{7-12}$=I). 4 (1.00 g, 2.80 mmol) was dissolved in anhydrous 1,2-dichloroethane (30 mL). ICl (29.15 mL, 1M in dichloromethane, 29.0 mmol) was added dropwise with stirring, and the reaction was allowed to run overnight at room temperature. The solvent was removed by rotary evaporator, and water was added to the dry residue. The mixture was precipitated with $N(CH_3)_4BF_4$ (0.48 g, 2.98 mmol). The filtrate was combined with 5% NaOH and an additional portion of an aqueous $N(CH_3)_4BF_4$ solution was added to precipitate any remaining anion. Both precipitated solids were filtered and dried. Yield: 2.6 g (93%).

Example 7

$[1,7,8,9,10,11,12-(CH_3)_7-CB_{11}H_5]N(CH_3)_4$ (6) ($R_{1,7-12}$= methyl). 5 (2.6 g, 2.62 mmol) was dissolved in dry THF (100 mL) and $CH_3MgI$ (24 mL, 3M in diethyl ether, 72.0 mmol) was added dropwise at −20° C. After the addition of the Grignard reagent, $(Ph_3P)_2PdCl_2$ catalyst (1.0 g, 1.42 mmol) was added and the mixture was refluxed overnight. This procedure was repeated twice with the same mount of Grignard reagent and catalyst. After 96 h a large, black, stone-like object filled the reaction flask. The mixture was evaporated and the dry black stone was dissolved in acetone. The solution was filtered, a portion of silica gel was added to the filtrate, and the acetone was distilled off. The residual saturated silica gel was placed on the top of a short silica column and was washed by benzene to remove the black mud. Once the black color disappeared, the column was washed with $CHCl_3:CH_3CN$ (2:1) without any separation. The crude mixture was finally separated on a column (50×2 cm) with $CHCl_3:CH_3CN$ (3:1). Ten fractions containing boron compounds were combined ($^{11}B$ NMR matched), dried, and precipitated. Yield: 1.05 g of a mixture of the starting compound 5 and the product 6. To react more of the residual starting material, the process of the addition of the Grignard reagent and catalyst was repeated, using the crude product from the previous step (1.05 g) with $CH_3MgI$ (2.92 ml, 8.76 mmol), and the Pd catalyst (0.117 g, 0.17 mmol). After refluxing overnight, the mixture was allowed to come to room temperature and was poured over ice (50 g). The THF was removed by rotary evaporation. The remaining water solution was acidified with 4M HCl (10 mL) and extracted into diethyl ether. It was then stirred with ether (10 mL) overnight, the ether was removed, and the water layer was reextracted three times with 10 mL ether portions. The ether washes were combined and dried by rotary evaporation. The residue was dissolved in 5% NaOH (30 mL). $N(CH_3)_4BF_4$ (0.44 g, 2.70 mmol) was dissolved in a minimal amount of water and added to the basic solution. The mixture was allowed to precipitate overnight, and was then filtered and dried thoroughly. Yield after recrystallization: 0.41 g (50%).

Example 8

$[1,7,8,9,10,11,12-(CH_3)_7-2,3,4,5,6-I_5-CB_{11}]N(CH_3)_4$ (7) ($R_{1,7-12}$=methyl, $R_{4-6}$=I). A small amount of 6 (a few mg) was dissolved in dry 1,2-dichloroethane (20 mL) under a nitrogen atmosphere, and ICl (6.35 mL, 1M in dichloromethane, 6.35 mmol) was added dropwise with stirring. The reaction mixture was stirred for 48 h at room temperature. The product was not isolated and was only characterized spectrally.

Example 9

$CB_{11}(CH_3)_{12}H_3O$ (1) ($R_{1-12}$=methyl). 6 (0.132 g, 0.42 mmol) was dissolved in dry 1,2-dichloroethane (30 mL) under a nitrogen atmosphere. Methyl trifluoromethanesulfonate (0.52 mL, 4.60 mmol) was added dropwise at room temperature with stirring. The mixture was stirred and refluxed at 110° C. for 72 h. It was then rotary evaporated, the residue was dissolved in $CHCl_3:CH_3CN$ (1:5), and chromatographed on a silica gel column with $CHCl_3:CH_3CN$ (5:1). In the process, cation exchange occurred and the $H_3O^+$ salt was isolated.

Example 10

$CB_{11}(CH_3)_{12}PPh_4^+$ (1) ($R_{1-12}$=methyl). $(1-CH_3-CB_{11}H_{11})N(CH_3)_4$ (3) (1.65 g, 7.14 mmol), $CaH_2$ (4.5 g, 108 mmol), 2,6-di-t-butylpyridine (17.9 g, 93.7 mmol), and methyl triflate (27.9 g, 170 mmol) were stirred under Ar at 0° C. for 10 hrs and then at 25° C. for 36 hrs, filtered, quenched with 5% NaOH, extracted with $Et_2O-Me_2CO$ (70/30), and dried over $MgSO_4$. 2,6-Di-t-butylpyridine was recovered by vacuum distillation, the residue dissolved in MeOH, passed through methanolic Amberlyst XN-1010 (acid form), treated with methanolic $PPh_4Cl$ (4 g, 10.7 mmol), and crystallized from MeOH. The yield was 48%.

We claim:

1. A compound which is a closo-carborate anion having the formula $CB_{11}H_{(n+1)-x}R_1R_2R_x^{1-}$ wherein n is an integer from 5 to 13 x is an integer from 1 to n+1, and wherein each $R_x$, independent of each other $R_x$, is selected from the group consisting of a hydrocarbon, a halogenated-hydrocarbon, and a halogen substituent, and wherein at least two of $R_x$ are hydrocarbon or halogenated-hydrocarbon substituents, or a salt thereof.

2. A compound according to claim 1 wherein n is 5 or 6.

3. A compound according to claim i wherein n is 7 or 8.

4. A compound according to claim 1 wherein n is 9.

5. A compound according to claim 1 wherein n is 10.

6. A compound according to claim 1 wherein n is 11 or 12 or 13.

7. A compound according to claim 1 wherein each R is methyl.

8. A compound according to claim 1 wherein each R is ethyl.

9. A compound according to claim 1 wherein each R is trifluoromethyl.

10. A compound according to claim 1 wherein each R is 2,2,2,-trifluoroethyl.

11. A compound according to claim 1 wherein n is 11, x is 12, $R_1$ and $R_7$–$R_{12}$ are each methyl, and $R_2$–$R_6$ are each hydrogen.

12. A compound according to claim 1 wherein n is 11, x is 12, $R_1$ and $R_7$–$R_{12}$ are each methyl, and $R_2$–$R_6$ are each ethyl.

13. A compound according to claim 1 wherein n is 11, x is 12, $R_1$ is ethyl and $R_2$–$R_{12}$ are each methyl.

14. A compound according to claim 1 which is a closo-carborate anion of the formula $CB_{11}Me_{12}^{1-}$.

15. The lithium salt of a compound of claim 1.

16. A compound which is a closo-borate anion having the formula $B_nH_{(n-x)}R_1R_2R_3 \ldots R_x^{2-}$ wherein n is an integer from 6 to 14, x is an integer from 1 to n, and wherein each $R_x$, independent of each other $R_x$, is selected from the group consisting of a hydrocarbon, a halogenated-hydrocarbon, and a halogen substituent, and wherein at least three of $R_x$ are hydrocarbon or halogenated-hydrocarbon substituents, or a salt thereof.

17. The compound according to claim 16 wherein n is 12.

18. The compound according to claim 16 wherein each R is a methyl, ethyl, a trifluoromethyl or a 2,2,2-trifluoroethyl.

19. A compound which is a hemicloso-carboranyl radical of the formula $CB_nH_{(n+1)-x}R_1R_2 \ldots R_x^{\bullet}$ wherein n is an integer from 5 to 13, x is an integer from 1 to n+1, and wherein each $R_x$, independent of each other $R_x$, is selected from the group consisting of a hydrocarbon, a halogenated-hydrocarbon, and a halogen substituent, and wherein at least two of $R_x$ are hydrocarbon or halogenated-hydrocarbon substituents.

20. A compound according to claim 19 whereto n is 5.

21. A compound according to claim 19 wherein n is 6.

22. A compound according to claim 19 wherein n is 7.

23. A compound according to claim 19 wherein n is 8.

24. A compound according to claim 19 wherein n is 9.

25. A compound according to claim 19 wherein n is 10.

26. A compound according to claim 19 wherein n is 11 or 12 or 13.

27. A compound according to claim 19 wherein each R is a methyl, ethyl, a trifluoromethyl or a 2,2,2-trifluoroethyl.

28. A compound according to claim 19 which is a hemicloso-carboranyl radical of the formula $CB_{11}Me_2^{\bullet}$.

29. A compound which is a hemicloso-boranyl radical anion having the formula $B_nH_{(n-x)}R_1R_2R_3 \ldots R_x^{\bullet 1-}$ wherein n is an integer from 5 to 14, x is an integer from 1 to n, and wherein each $R_x$, independent of each other $R_x$, is selected from the group consisting of a hydrocarbon, a halogenated-hydrocarbon, and a halogen substituent, or a salt thereof.

30. A compound according to claim 29 which is a hemicloso-boranyl radical of the formula $B_{12}Me_{12}^{\bullet 1-}$.

31. A method for synthesizing a compound selected from the group consisting of: a closo-carborate anion of the formula $CB_nH_{(n+1)-x}R_x^{1-}$ wherein n is an integer from 5 to 13 and x is an integer from 2 to n+1; a closo-borate anion of the formula $B_nH_{(n-x)Rx}^{2-}$ wherein n is an integer from 6 to 14 and x is an integer from 2 to n; a hemicloso-carboranyl radical of the formula $CB_nH_{(n+1)-x}R_x^{\bullet}$ wherein n is an integer from 5 to 13 and x is an integer from 2 to n+1; and a hemicloso-boranyl radical of the formula $B_nH_{(n-x)}R_x^{\bullet 1-}$ wherein n is an integer from 5 to 14 and x is an integer from 2 to n, and wherein each R, independent of each other R, is selected from the group consisting of hydrocarbon, halogenated-hydrocarbon and halogen substituents, said method comprising the steps of:

a) reacting in a solvent a mono-substituted closo-carborate anion of the formula $CB_nH_nR^{1-}$ wherein R is covalently bound to C and wherein R is a hydrocarbon, a halogenated-hydrocarbon or a halogen substituent or a closo-borate anion of the formula $B_nH_n^{2-}$, with a strong alkylating agent, wherein a means to remove acid is included in this step when the reaction generates acid, thereby generating said closo-carborate anion or closo-borate anion, and for the synthesis of said radicals, said method further comprises the step of:

b) chemically or electrochemically oxidizing said anion, thereby generating said hemicloso-carboranyl radical or hemicloso-boranyl radical.

32. A method according to claim 31 wherein the mono-substituted closo-carborate anion is obtained by a method comprising the steps:

a) reacting in a solvent a compound which is a closo-carborate anion of the formula $CB_nH_{(n+1)}^{1-}$, a strong base, an alkylating reagent, and b) thereafter isolating said mono-substituted closo-carborate anion.

* * * * *

UNITED STATES PATENT AND TRADEMARK OFFICE
CERTIFICATE OF CORRECTION

PATENT NO. : 5,731,470

DATED : March 24, 1998

INVENTOR(S) : Michl et al.

It is certified that error appears in the above-identified patent and that said Letters Patent is hereby corrected as shown below:

In column 1, line 37, rewrite "384-386" as --384-386;--.

In column 2, line 30, rewrite "mine" as --amine--.

In column 2, Table 1, 3$^{rd}$ entry of 8 vertices, replace "$CB_8Y_8^{1-}$" with --$CB_7Y_8^{1-}$--.

In column 3, Table 1, 3$^{rd}$ entry of 9 vertices, replace "$CB_9H_9^{1-}$" with --$CB_8H_9^{1-}$--.

In column 3, Table 1, 3$^{rd}$ entry of 10 vertices, replace "$CB_{10}Y_{10}^{1-}$" with --$CB_9H_{10}^{1-}$--.

In column 3, Table 1, 2$^{nd}$ entry of 11 vertices, replace "$B_{10}Y_{11}^{1-}$" with --$B_{11}Y_{11}^{1-}$--.

In column 4, line 44, replace "akyl" with --alkyl--.

In column 7, line 37, delete "$CH_3\text{-}CH_{2=CH\text{-}CH=CH2}\text{-})$." and replace with --$CH_3\text{-}CH_2\text{=}CH\text{-}CH\text{=}CH_2)$.--

In column 8, line 3, replace "goups" with --groups--.

In column 8, line 32, replace "or-branched" with --α-branched--.

In column 9, line 26, replace "$R_2$" with --$R_{12}$--.

In column 9, line 32, replace "$R_2$" with --$R_{12}$--.

In column 9, line 55, replace "$R_2$" with --$R_{12}$--.

In column 9, line 56, replace "$R_2$" with --$R_{12}$--.

In column 10, line 7, replace "$CB_{11}Me_2^{\bullet}$" with --$CB_{11}Me_{12}^{\bullet}$--.

In column 11, line 56, replace "prepared" with --prepare--.

UNITED STATES PATENT AND TRADEMARK OFFICE
CERTIFICATE OF CORRECTION

PATENT NO.   : 5,731,470

DATED        : March 24, 1998

INVENTOR(S)  : Michel et al.

It is certified that error appears in the above-identified patent and that said Letters Patent is hereby corrected as shown below:

In column 12, line 29, replace "mount" with --amount--.

In column 13, line 10, between "such" and "calcium" insert --as--.

In column 13, line 30, replace "$R_{.12}$" with --$R_{1-12}$--.

In column 13, line 59, delete "lo" between "specifically" and "exemplified".

In column 13, line 65, replace "$CB_{11},H_{12}^-$" with $CB_{11}H_{12}^{1-}$--.

In column 15, line 31, replace "dedecaborate" with --dodecaborate--.

In column 15, line 52, replace "$(CH_3)_{12}CB_{11}$" with --$(CH_3)_{12}CB_{11}^{1-}$--.

In column 18, line 8, replace "12" with --$I_2$--.

In column 18, line 14, replace "$(CH_3)_3N.HCl$" with --$(CH_3)_3N \cdot HCl$--.

In column 18, line 34, replace "$(CH_3)_3N.HCl$" with --$(CH_3)_3N \cdot HCl$--.

In column 18, line 35, replace "mount" with --amount--.

In column 18, line 50, replace "mount" with --amount--.

In column 19, line 37, replace "$N(CH_3)4BF4$" with --$N(CH_3)_4BF_4$--.

In column 19, line 50, replace "mount" with --amount--.

UNITED STATES PATENT AND TRADEMARK OFFICE
CERTIFICATE OF CORRECTION

PATENT NO. : 5,731,470

DATED : March 24, 1998

INVENTOR(S) : Michl et al.

It is certified that error appears in the above-identified patent and that said Letters Patent is hereby corrected as shown below:

<u>In the claims</u>:

In claim 1, column 20, line 55, rewrite "$CB_{11}H_{(n+1)-x}R_1R_2R_x^{1-}$" as --$CB_nH_{(n+1)-x}R_1R_2...R_x^{1-}$--.

In claim 1, column 20, line 56, rewrite "5 to 13" as --5 to 13,--.

In claim 3, column 20, line 63, rewrite "claim i" as --claim 1--.

In claim 14, column 21, line 18, rewrite "$CB_{11}Me_{12}^{1}$" as --$CB_{11}Me_{12}^{1-}$--.

In claim 31, column 22, line 15, rewrite "$B_nH_{(n-x)Rx}^{2-}$" as --$B_nH_{(n-x)}R_x^{2-}$--.

Signed and Sealed this

Fifteenth Day of September, 1998

Attest:

BRUCE LEHMAN

Attesting Officer

Commissioner of Patents and Trademarks